United States Patent
Ortiz et al.

(10) Patent No.: US 8,029,535 B2
(45) Date of Patent: Oct. 4, 2011

(54) FASTENERS FOR USE WITH GASTRIC RESTRICTION

(75) Inventors: Mark S. Ortiz, Milford, OH (US); Michael J. Stokes, Cincinnati, OH (US); David N. Plescia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 881 days.

(21) Appl. No.: 11/197,529

(22) Filed: Aug. 5, 2005

(65) Prior Publication Data

US 2007/0032822 A1    Feb. 8, 2007

(51) Int. Cl.
*A61B 17/04* (2006.01)
*A61B 17/08* (2006.01)
*A61B 17/10* (2006.01)

(52) U.S. Cl. .............. 606/232; 606/153; 227/175.1
(58) Field of Classification Search ............. 606/219, 606/213, 151, 232, 153, 223
See application file for complete search history.

(56) References Cited

U.S. PATENT DOCUMENTS

| | | | | |
|---|---|---|---|---|
| 4,217,902 A | * | 8/1980 | March | 606/221 |
| 4,535,772 A | * | 8/1985 | Sheehan | 606/218 |
| 5,047,047 A | * | 9/1991 | Yoon | 606/216 |
| 5,080,663 A | | 1/1992 | Mills et al. | |
| 5,242,457 A | * | 9/1993 | Akopov et al. | 606/144 |
| 5,304,204 A | * | 4/1994 | Bregen | 606/219 |
| 5,376,101 A | | 12/1994 | Green et al. | |
| 5,437,681 A | | 8/1995 | Meade et al. | |
| 5,462,558 A | | 10/1995 | Kolesa et al. | |
| 5,514,159 A | | 5/1996 | Matula et al. | |
| 5,540,705 A | | 7/1996 | Meade et al. | |
| 5,571,119 A | | 11/1996 | Atala | |
| 5,709,693 A | | 1/1998 | Taylor | |
| 5,713,910 A | | 2/1998 | Gordon et al. | |
| 5,814,071 A | | 9/1998 | McDevitt et al. | |
| 6,036,694 A | | 3/2000 | Goble et al. | |
| 6,346,111 B1 | | 2/2002 | Gordon et al. | |
| 6,443,962 B1 | | 9/2002 | Gaber | |
| 6,454,778 B2 | | 9/2002 | Kortenbach | |
| 6,494,888 B1 | | 12/2002 | Laufer et al. | |
| 6,506,196 B1 | | 1/2003 | Laufer | |
| 6,558,400 B2 | | 5/2003 | Deem et al. | |
| 6,599,311 B1 | * | 7/2003 | Biggs et al. | 606/232 |
| 6,607,542 B1 | * | 8/2003 | Wild | 606/157 |
| 6,656,194 B1 | | 12/2003 | Gannoe et al. | |
| 6,663,639 B1 | | 12/2003 | Laufer et al. | |
| 6,719,763 B2 | | 4/2004 | Chung et al. | |
| 6,719,764 B1 | | 4/2004 | Gellman et al. | |
| 6,746,460 B2 | | 6/2004 | Gannoe et al. | |
| 6,755,843 B2 | | 6/2004 | Chung et al. | |
| 6,773,440 B2 | | 8/2004 | Gannoe et al. | |
| 6,835,200 B2 | | 12/2004 | Laufer et al. | |
| 6,908,427 B2 | | 6/2005 | Fleener et al. | |
| 6,923,819 B2 | | 8/2005 | Meade et al. | |

(Continued)

FOREIGN PATENT DOCUMENTS

EP    702934    3/1996

(Continued)

*Primary Examiner* — Corrine M McDermott
*Assistant Examiner* — Christina Lauer (57) ABSTRACT

A fastener is used during endoscopic procedures in which a suture is used in creating a predefined pouch through tissue apposition within the stomach. The fastener includes a fastener body having a tissue anchor for selectively securing the fastener body to tissue. The fastener body also includes a connection aperture shaped and dimensioned for passage of a suture therethrough.

3 Claims, 7 Drawing Sheets

U.S. PATENT DOCUMENTS

| | | |
|---|---|---|
| 2002/0022851 A1 | 2/2002 | Kalloo et al. |
| 2002/0107530 A1 | 8/2002 | Sauer et al. |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0006351 A1 | 1/2004 | Gannoe et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto |
| 2004/0147958 A1 | 7/2004 | Lam et al. |
| 2004/0162568 A1 | 8/2004 | Saadat |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2004/0267312 A1* | 12/2004 | Kanner et al. ............... 606/219 |
| 2005/0004575 A1* | 1/2005 | Sgro et al. ................. 606/72 |
| 2005/0015101 A1 | 1/2005 | Gibbens, III et al. |
| 2005/0055038 A1 | 3/2005 | Kelleher et al. |
| 2005/0075653 A1 | 4/2005 | Saadat et al. |
| 2005/0107812 A1* | 5/2005 | Starksen et al. ............ 606/143 |

FOREIGN PATENT DOCUMENTS

| | | |
|---|---|---|
| EP | 1545336 | 6/2005 |
| EP | 1569709 | 9/2005 |
| WO | WO 00/61012 | 10/2000 |
| WO | WO 01/10312 | 2/2001 |
| WO | WO 01/66001 | 9/2001 |
| WO | WO 01/89366 | 11/2001 |
| WO | WO 02/35980 | 5/2002 |
| WO | WO 2005/020802 | 3/2005 |

* cited by examiner

FASTENERS FOR USE WITH GASTRIC RESTRICTION

BACKGROUND OF THE INVENTION

1. Field of the Invention

The present invention relates to gastric reduction surgery. More particularly, the invention relates to fasteners specifically adapted for use during endoscopic gastric reduction surgery.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most commonly performed procedure is Roux-en-Y gastric bypass (RYGB). This procedure is highly complex and is commonly utilized to treat people exhibiting morbid obesity. However, and with this in mind, around 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety. Another commonly employed gastric reduction procedure is vertical gastroplasty. This procedure is achieved by applying a series of horizontal sutures to create an incomplete horizontal line defining a small fundic pouch for restriction of food ingestion. This procedure is commonly performed laparoscopically and as such requires substantial preoperative, operative, postoperative resources.

Regardless of the procedure employed, many gastric reduction procedures require that a suture(s) be installed, creating a defined region through which nourishment may pass and restricting oral intake. The sutures used during these procedures are commonly secured to the stomach wall through the implementation of fasteners provided with openings through which the suture may be passed in securing the same within the stomach wall. By passing the suture through a series of properly positioned fasteners, one is able to create a pouch of predefined dimensions within the stomach of an individual. With this in mind, problems associated with gastric reduction surgery hinge heavily upon the issue of tissue apposition, grasping and control.

Since such procedures are relatively new and the associated fasteners have yet to be fully developed for the specific problems encountered during gastric reduction procedures, a need exists for new fasteners designed to optimally function during gastric reduction procedures. Such fasteners must provide for maintaining tissue apposition, fastening and controlling tissue in a manner which prevents erosion of sutures through the stomach wall and provide predictable depth of penetration through the stomach wall. The present invention provides such a variety of fasteners specifically adapted for gastric reduction procedures through tissue apposition.

SUMMARY OF THE INVENTION

It is, therefore, an object of the present invention to provide a fastener for use during endoscopic procedures in which a suture is used in creating a predefined pouch through tissue apposition within the stomach. The fastener includes a fastener body having a tissue anchor for selectively securing the fastener body to tissue. The fastener body also includes a connection aperture shaped and dimensioned for passage of a suture therethrough.

It is also an object of the present invention to provide a fastener wherein the fastener body is substantially W-shaped.

It is another object of the present invention to provide a fastener wherein the fastener body includes first and second C-shaped segments extending from the connection aperture.

It is a further object of the present invention to provide a fastener wherein the fastener body includes first, second and third anchors extending downwardly therefrom and first and second actuation wings.

It is also an object of the present invention to provide a fastener wherein the fastener body includes a barbed anchor with a retractable tip.

It is also another object of the present invention to provide a fastener wherein the fastener body is composed of a resilient, elongated member, the elongated member includes a first end and a second end. The first and second ends are pointed for piercing tissue upon application. The elongated member includes a first closed loop and a second loop created by alignment of the first end and the second end of the elongated member.

It is still another object of the present invention to provide a fastener wherein the fastener body is composed of first and second semi-circular loops interrelated for closure and locking within the tissue of an individual.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Referring to the various figures, a variety of fasteners are disclosed in accordance with the present invention. The fasteners are particularly adapted for use during endoscopic procedures in which a suture is used in creating a predefined pouch through tissue apposition within the stomach (or other hollow organ) of an individual.

Figure 1:
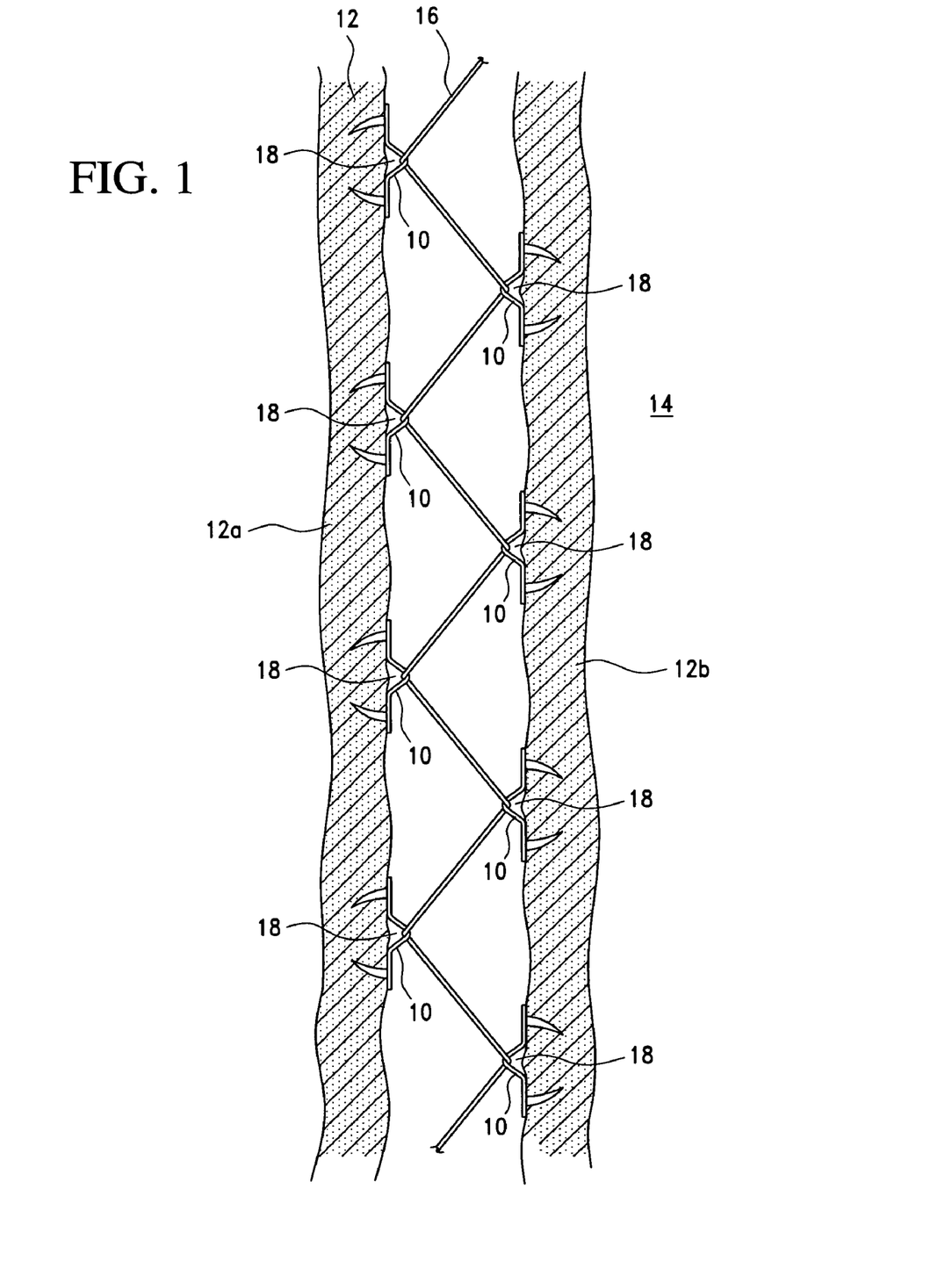
FIG. 1 is a cross-sectional view showing the use of fasteners in gastric reduction surgery.

Generally, and with reference to FIG. 1, a series of fasteners 10 are secured along the gastric wall 12 in a predetermined configuration. For example, the fasteners 10 may be applied vertically along the stomach 14 creating a fastener arrangement necessary to ultimately form a mattress stitch pattern. Although a mattress stitch pattern is disclosed in accordance with a preferred embodiment of the present invention, those skilled in the art will appreciate that other stitch patterns may be employed in accordance with a preferred embodiment of the present invention. The exact direction in which the fasteners are applied is not critical, and medical practitioners may apply the fasteners in a direction and order which best suits the specific patient. For example, the fasteners 10 may be applied to the gastric wall 12 alternating between the anterior wall 12a and posterior wall 12b of the stomach 14 as an applicator is moved distally to proximally or vice versa.

Once the fasteners 10 are properly applied along the gastric wall 12, the suture 16 is strung through a connection aperture 18 within the fastener 10 and connected to the fasteners 10. In accordance with a preferred embodiment, the suture 16 is strung to create a mattress stitch pattern within the stomach 14 in a substantially vertical direction extending distally and proximally within the stomach 14. Once all of the fasteners 10 are placed along the gastric wall 12 and the suture 16 is strung through the connection apertures 18 of the fasteners 10 in a mattress stitch pattern, the suture 16 may be pulled taut to bring the gastric walls 12a, 12b into approximation with each other.

The resulting structure of the stomach 14 is that of a tubular member connecting the esophagus to the pylorus with the gastric remnant allowed to pass gastric acid into the food stream. This produces a smaller stomach volume as well as a restrictive means for the bolus.

The various fasteners disclosed in accordance with the present invention are intended as two stage deployment devices. In particular, the first stage of the deployment is to pierce the tissue with the tips of the fastener (the fastener being loaded into the applicator and stage one deployment is performed with the fastener in a deformed or loaded position). The second stage of deployment, that is, stage two deployment, consists of releasing the application mechanism responsible for maintaining the aforementioned loaded position of the fastener, thereby allowing the fastener to spring into its natural position. Upon fastener translation into the natural position, the tips of the fastener both pierce deeper into the tissue as well as push the tissue up into the apex of the fastener thereby capturing the suture in a semi-stable position.

Figure 2:
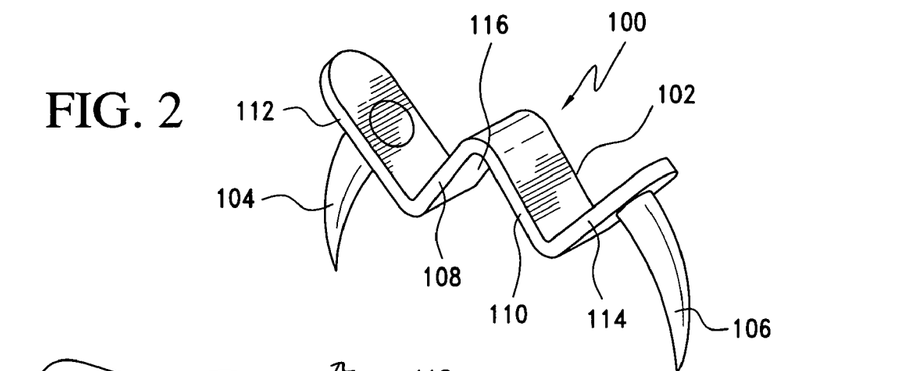
FIGS. 2, 3 and 4 disclose a first fastener embodiment in accordance with the present invention.
Figure 3:
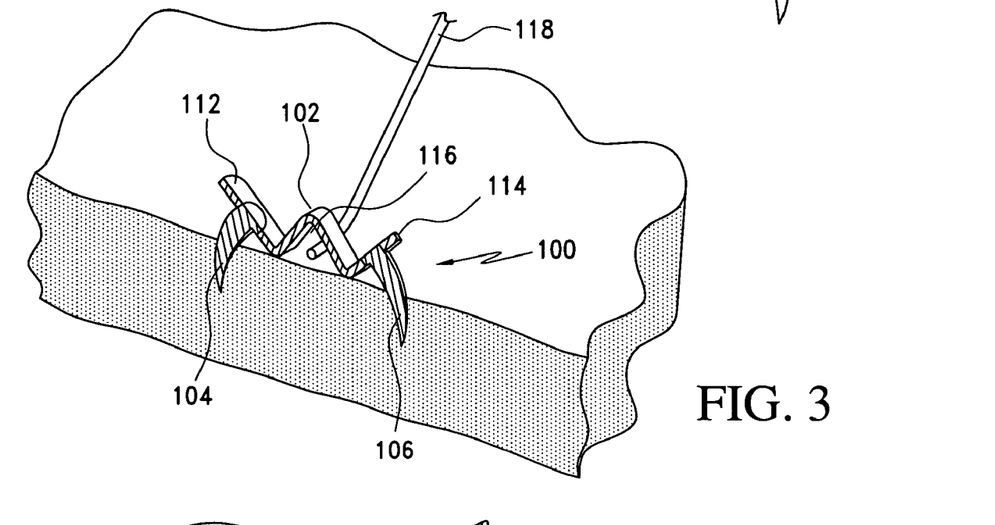
Figure 4:
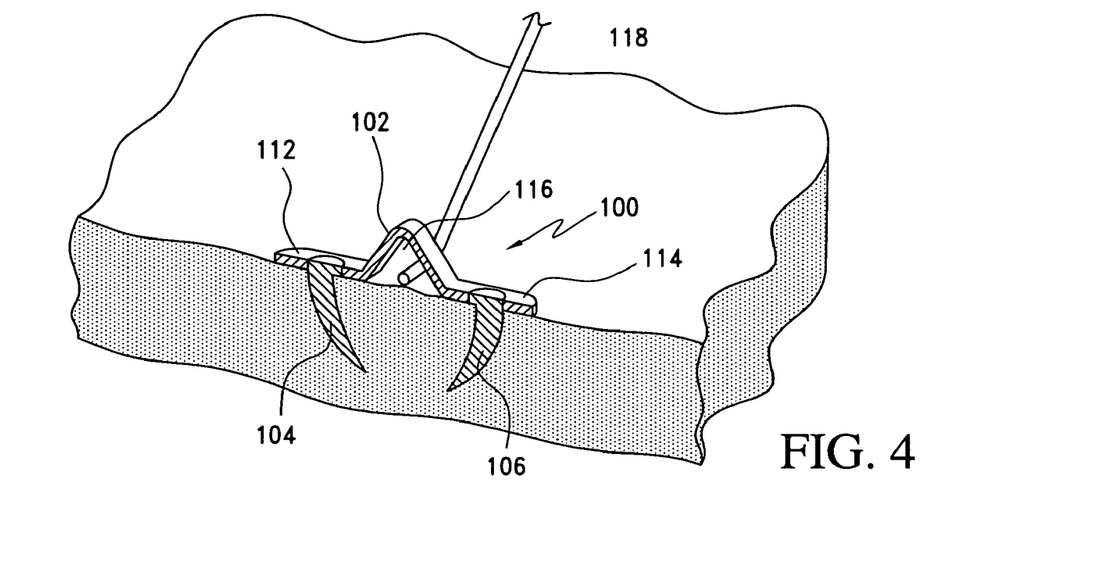

Referring to FIGS. 2, 3 and 4, a first embodiment in accordance with the present invention is disclosed. The fastener 100 includes a substantially W-shaped main body 102 with first and second anchors 104, 106 depending therefrom. In particular, the main body 102 includes four angularly oriented segments 108, 110, 112, 114 which are adapted for relative movement to achieve the goals of the present invention. The inner first and second segments 108, 110 are coupled to create an apex or opening 116 in which the suture 118 is securely contained. The outer third and fourth segments 112, 114 respectively extend from the first and second segments 108, 110 and support respective anchors therefrom. In accordance with a preferred embodiment of the present invention, the anchors 104, 106 are curved members extending from the third and fourth segments 112, 114 in a manner optimizing secure attachment upon actuation thereof.

In practice, the fastener 100 is spring biased, and held, to an orientation substantially as shown in FIG. 3 with the third and fourth segments 112, 114 drawn toward the first and second segments 108, 110, and the tips of the first and second anchors 104, 106 substantially parallel to each other. The fastener 100 is held in this orientation by an applicator. With this in mind, the fastener 100 is held in this position until it is driven into the stomach tissue at a desired location with the anchors 104, 106 perpendicularly inserted within the tissue. Once properly positioned as shown in FIG. 4, the fastener 100 is released by the applicator and the outer third and fourth segments 112, 114 of the fastener 100 are permitted to swing away from the respective first and second segments 108, 110 toward the tissue of the individual. The tips of the anchors 104, 106, therefore, spring toward one another and the fastener 100 ultimately pinches tissue within the anchors 104, 106. With the anchors 104, 106 securely held within the tissue and the first and second segments 108, 110 defining an apex 116 in which the suture 118 is held, the suture 118 is securely supported relative to the tissue of the individual undergoing the procedure.

Figure 5:
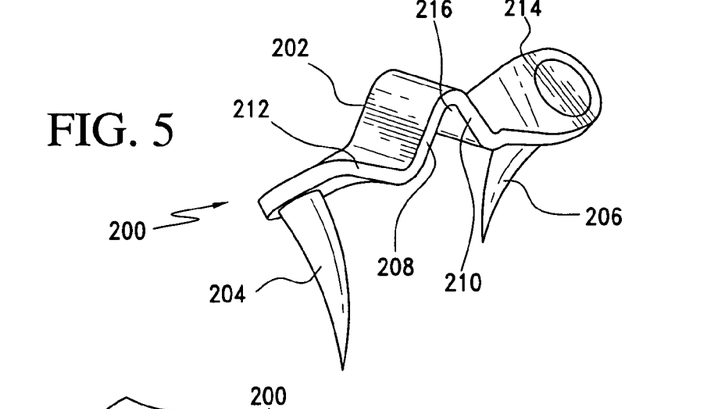
FIGS. 5, 6 and 7 show another embodiment of a fastener in accordance with the present invention.
Figure 6:
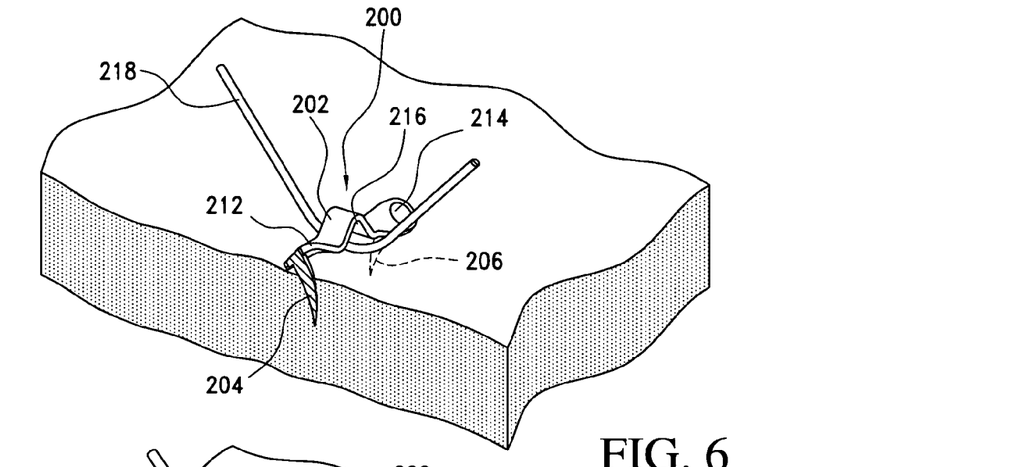
Figure 7:
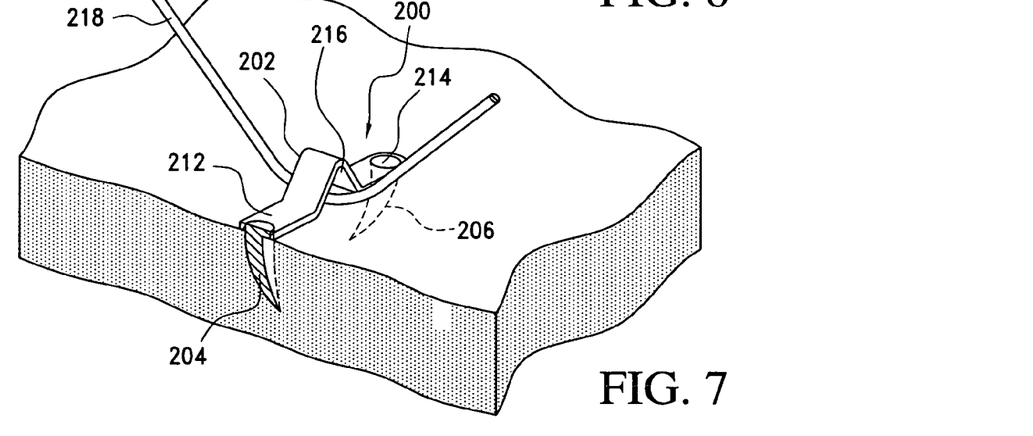

Referring to FIGS. 5, 6 and 7, a second embodiment of a fastener 200 in accordance with the present invention is disclosed. The fastener 200 includes a substantially W-shaped main body 202 with first and second anchors 204, 206 depending therefrom. In particular, the main body 202 includes four angularly oriented segments 208, 210, 212, 214 which are adapted for relative movement to achieve the goals of the present invention. The inner first and second segments 208, 210 are coupled to create an apex or opening 216 in which the suture 218 is securely contained. The outer third and fourth segments 212, 214 respectively extend from the first and second segments 208, 210 and support respective anchors 204, 206 therefrom. In accordance with a preferred embodiment of the present invention, the anchors 204, 206 are curved members extending from the third and fourth segments 210, 212 in a manner optimizing secure attachment upon actuation thereof.

In practice, the fastener 200 is spring biased to an orientation substantially as shown in FIG. 6, with the third and fourth segments 212, 214 torsionally rotated relative to the first and second segments 208, 210 and along the longitudinal axes of the respective third and fourth segments 212, 214. The fastener 200 is held in this orientation by an applicator. When the fastener 200 is oriented in this biased configuration, the tips of the first and second anchors 204, 206 are substantially parallel to each other. The fastener 200 is held in this position until it is driven into the stomach tissue at a desired location with the anchors 204, 206 perpendicularly inserted within the tissue. Once properly positioned as shown in FIG. 7, the fastener 200 is released by the applicator and the outer third and fourth segments 212, 214 of the fastener 200 are permitted to rotate relative to the respective first and second segments 208, 210, and about the longitudinal axes of the respective third and fourth segments 212, 214, toward the tissue of the individual. The tips of the anchors 204, 206, therefore, spring down into the tissue ultimately anchoring the fastener 200 within the tissue. With the anchors 204, 206 securely held within the tissue and the first and second segments 208, 210 defining an apex 216 in which the suture 218 is held, the suture 218 is securely supported relative to the tissue of the individual undergoing the procedure.

Figures 8, 9:
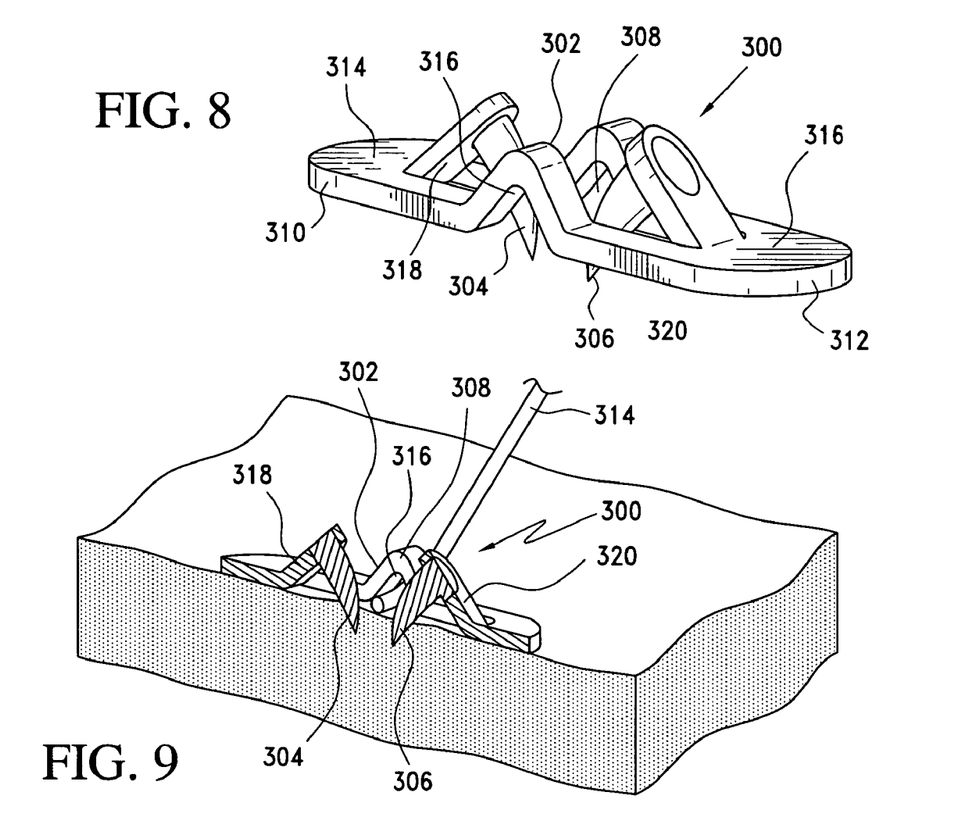
FIGS. 8, 9 and 10 show another embodiment of a fastener in accordance with the present invention.
Figure 10:
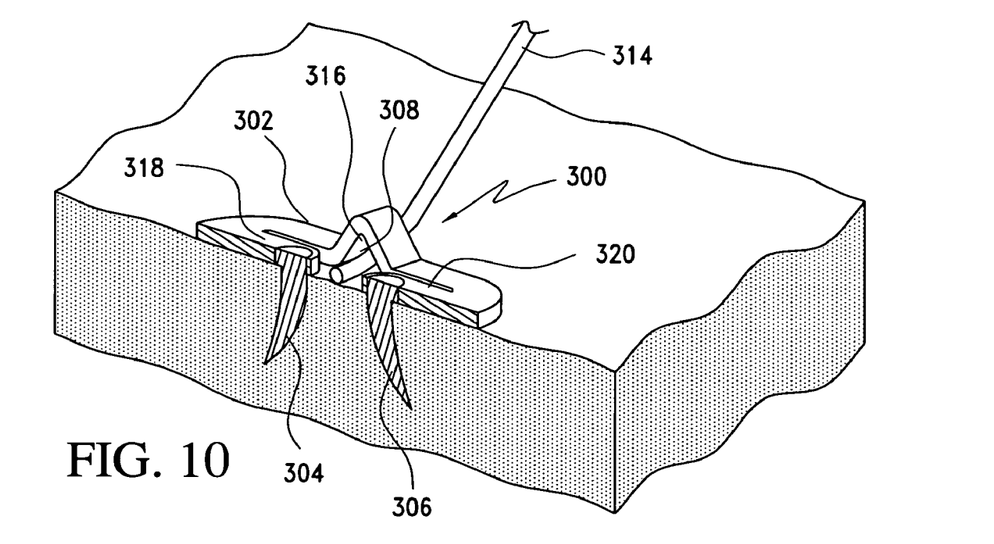

Referring to FIGS. 8, 9 and 10, a third embodiment of a fastener 300 in accordance with the present invention is disclosed. The fastener 300 includes a main body 302 with first and second anchors 304, 306 depending therefrom. In particular, the main body 302 includes a central aperture section 308 with first and second C-shaped segments 310, 312 extending therefrom. The central aperture section 308 is generally V-shaped and is shaped and dimensioned for the passage of a suture 314 once the fastener 300 is properly secured to the gastric tissue. The first and second C-shaped segments 310, 312 extend from opposite ends of the central aperture section 308 and lie in a plane which is substantially perpendicular to that of the V-shaped central aperture section 308. With this in mind, the first and second C-shaped segments 310, 312 are oriented to lie upon the tissue, forming a base for the fastener 300, while the central aperture section 308 is adapted to extend away from the tissue defining an opening 316 through which a suture 314 may pass.

Each of the C-shaped segments 310, 312 include a first leg 314, 318 and a second leg 316, 320 with the first leg 314, 318 coupled to the central aperture section 308 and the second leg 316, 320 extending substantially parallel thereto. The second legs 316, 320 of the respective first and second C-shaped segments 310, 312 each include a downwardly facing anchor 304, 306 extending therefrom. In accordance with a preferred embodiment of the present invention, the anchors 304, 306 are curved members extending from the second legs 316, 320 of the respective first and second C-shaped segments 310, 312 in a manner optimizing secure attachment upon actuation thereof.

In practice, the fastener 300 is spring biased to an orientation substantially as shown in FIG. 9 with the second legs 316, 320 of the first and second C-shaped segments 310, 312 drawn upwardly relative to the central aperture section 308 and the first legs 314, 318 of the respective first and second C-shaped segments 310, 312. The fastener 300 is held in this orientation by an applicator. In this orientation, the tips of the first and second anchors 304, 306 are substantially parallel to each other. With this in mind, the fastener 300 is held in this position until it is driven into the stomach tissue at a desired location with the anchors 304, 306 perpendicularly inserted within the tissue. Once properly positioned as shown in FIG. 10, the fastener 300 is released by the applicator and the second legs 316, 320 of the first and second C-shaped segments 310, 312 of the fastener 300 are permitted to swing downwardly toward the tissue of the individual. The tips of the anchors 304, 306, therefore, spring away from one another and the fastener 300 ultimately pinches tissue within the anchors 304, 306. With the anchors 304, 306 securely held within the tissue and the central aperture section 308 defining an apex 316 in which the suture 314 is held, the suture 314 is securely supported relative to the tissue of the individual undergoing the procedure.

Figure 11:
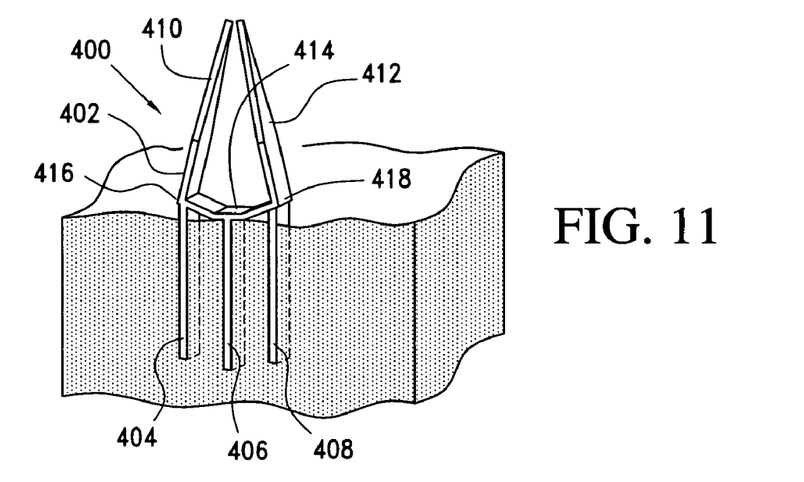
FIGS. 11, 12 and 13 show yet another embodiment of a fastener in accordance with the present invention.
Figure 12:
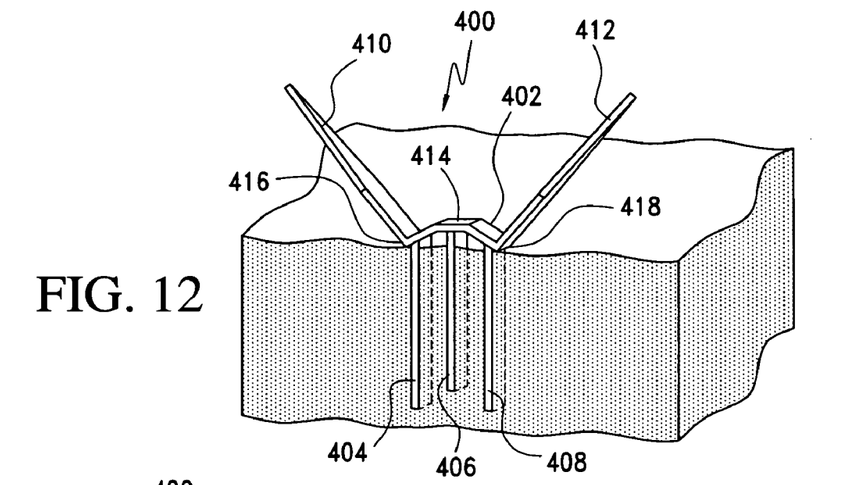
Figure 13:
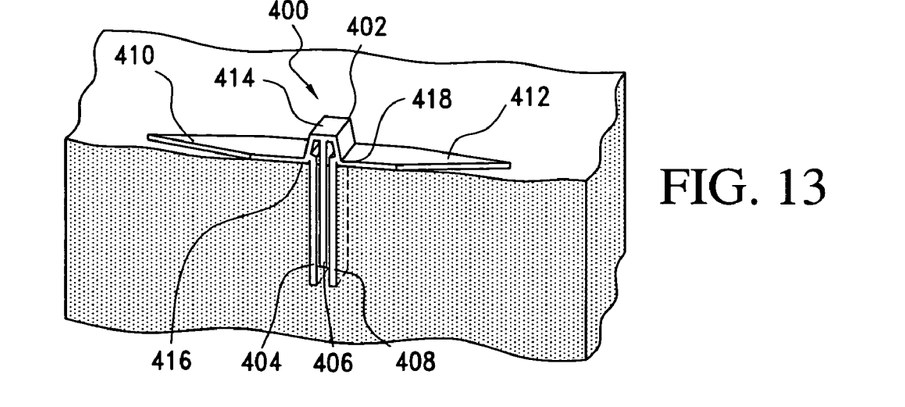

With regard to FIGS. 11, 12 and 13, a further embodiment of a fastener 400 in accordance with the present invention is disclosed. This embodiment includes a main body 402 with first, second and third anchors 404, 406, 408 extending downwardly therefrom. The main body 402 further includes a pair of actuation wings 410, 412 extending therefrom.

In particular, the main body 402 includes a central segment 414 which is resiliently biased for inversion from a concave configuration to a convex configuration in which the anchors 404, 406, 408 securely grip and couple to the tissue in which they are mounted. The central segment 414 includes a first end 416 and a second end 418. The first and second actuation wings 410, 412 respectively extend from the first and second ends 416, 418 of the central segment 414. The first and second actuation wings 410, 412 are secured to the central segment 414 in a manner permitting pivotal motion relative thereto. In this way, the first and second actuation wings 410, 412 are selectively rotated from an insertion position, in which they extend upwardly from the central segment 414, to a partially deployed state, in which they are oriented obliquely relative to the central segment 414, and finally to a fully deployed position, where they are substantially aligned with the central segment 414.

As the first and second actuation wings 410, 412 rotate from the insertion position to the fully deployed position, a fulcrum is created which causes the central segment 414 to undergo a change in shape from its concave configuration to its convex configuration. Movement of the central segment 414 between the concave configuration and the convex configuration causes the first, second and third anchors 404, 406, 408 to be drawn together in a manner facilitating coupling to the tissue.

As the central segment 414 moves between its convex configuration and its concave configuration, the anchors 404, 406, 408 are simultaneously drawn together in a manner that couples them to the tissue in which they are mounted. More particularly, when the fastener 400 is oriented in its initial insertion shape, with the first and second actuation wings 410, 412 extending therefrom and the central segment 414 in a concave configuration, the first, second and third anchors 404, 406, 408 extend downwardly into the tissue with the second anchor 406 extending the deepest within the tissue. As the actuation wings 410, 412 are rotated to their partially deployed position, the central segment 4 inverts to its convex configuration with the second anchor 406 being pulled upwardly and the first and third anchors 404, 408 being drawn toward the second anchor 406. As the first and second actuation wings 410, 412 move further toward the tissue, and the fastener 400 reaches its fully deployed orientation, the first and third anchors 404, 408 are further drawn toward each other, pinching the tissue therebetween and coupling the fastener 400 in position along the tissue.

Figures 14, 15, 16:
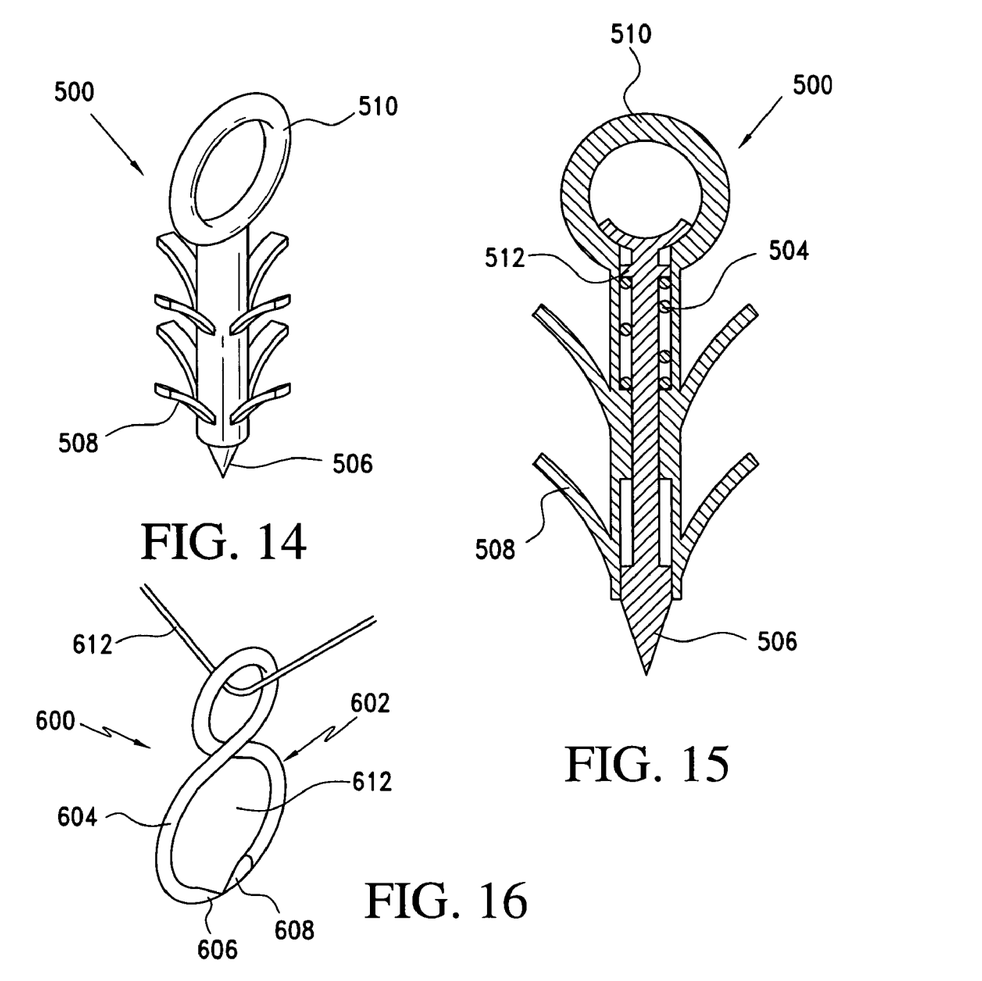
FIGS. 14 and 15 disclose yet still another embodiment of a fastener in accordance with the present invention.
FIGS. 16, 17 and 18 show another embodiment of a fastener in accordance with the present invention.

Referring to FIGS. 14 and 15, another embodiment of a fastener 500 in accordance with the present invention is disclosed. The fastener 500 includes a barbed anchor 508 with a retractable tip 506. The fastener also includes a loop 510 at its distal end. In practice, the retractable tip 506 is extended during penetration within the gastric tissue. A suture is placed through the loop 510 and the fastener 500 may, thereby, be applied to the tissue. As the anchor 508 penetrates the tissue with the tip 506 in its extended position, the barbs 512 along the anchor 508 hold the fastener 500 within the tissue in place. Once properly positioned the tip 506 may be retracted allowing for smoother penetration and reducing the possibility of damage to the tissue.

The tip 506 retraction of the fastener 500 is further achieved by incorporating a biasing spring 502 within the fastener body 504. The biasing spring 502 acts upon the tip shaft 512 forcing the tip 506 to a retracted positioned when the fastener 500 is not loaded within an applier.

Figure 17:
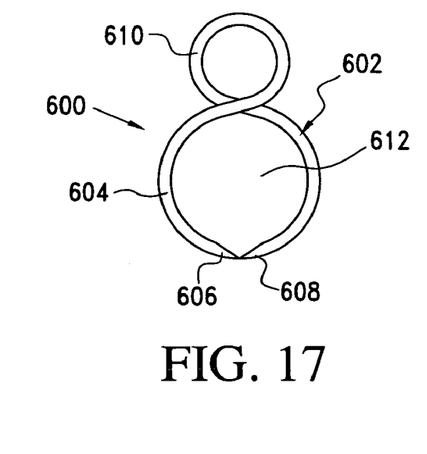
Figure 18:
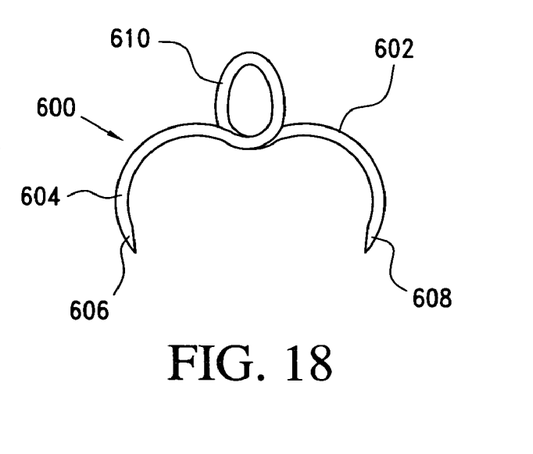

Referring to FIGS. 16, 17 and 18, a sixth embodiment of a fastener 600 in accordance with the present invention is disclosed. The fastener includes a main body 602 composed of a resilient, elongated member 604. The elongated member 604 includes a first end 606 and a second end 608. As will become apparent based upon the following disclosure, the first and second ends are pointed for piercing tissue upon application and functioning as anchors within the spirit of the present invention.

The elongated member 604 is generally formed in the shape of an "8" with a first closed loop 610 and a second loop 612 created by the alignment of the first and second ends 606, 608 of the elongated member 604. The first loop 610 is shaped and dimensioned for receiving a suture 612 passing therethrough. The second loop 612, with the first and second ends 606, 608 in a facing relationship is shaped and dimensioned for selective opening allowing for tissue to be "grabbed" and retained therein. With this in mind, the fastener 600 functions much like a spring loaded claw and, preferably, the tips thereof overlap.

The fastener 600 is designed such that it may be resiliently biased, pulling the first and second ends 606, 608 of the elongated member 604 away from each other prior to securing within the tissue and as such may be made of shape memory materials, for example, Nitinol. This creates an opening into which tissue may be positioned. Once the fastener 600 is properly positioned with tissue within the second loop 612, the fastener 600 may be released allowing the first and second ends 606, 608 of the elongated member 604 to move toward each other and securely couple the fastener 600 to the gastric tissue. That is, the fastener 600 is formed much like a "squeeze loop" in which squeezing the first loop 610 allows the anchors, that is, the first and second ends 606, 608 of the elongated member 604, to move apart permitting tissue to enter the space between the anchors 606, 608. Thereafter, release of the first loop 610 causes the anchors 606, 608 to spring toward each other capturing tissue and securing the fastener 600 to the tissue.

Figure 19:
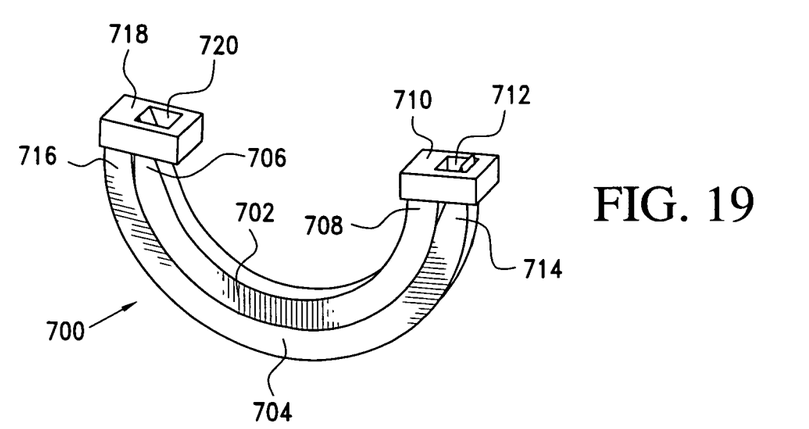
FIGS. 19, 20 and 21 show a further embodiment in accordance with the present invention.
Figures 20, 21:
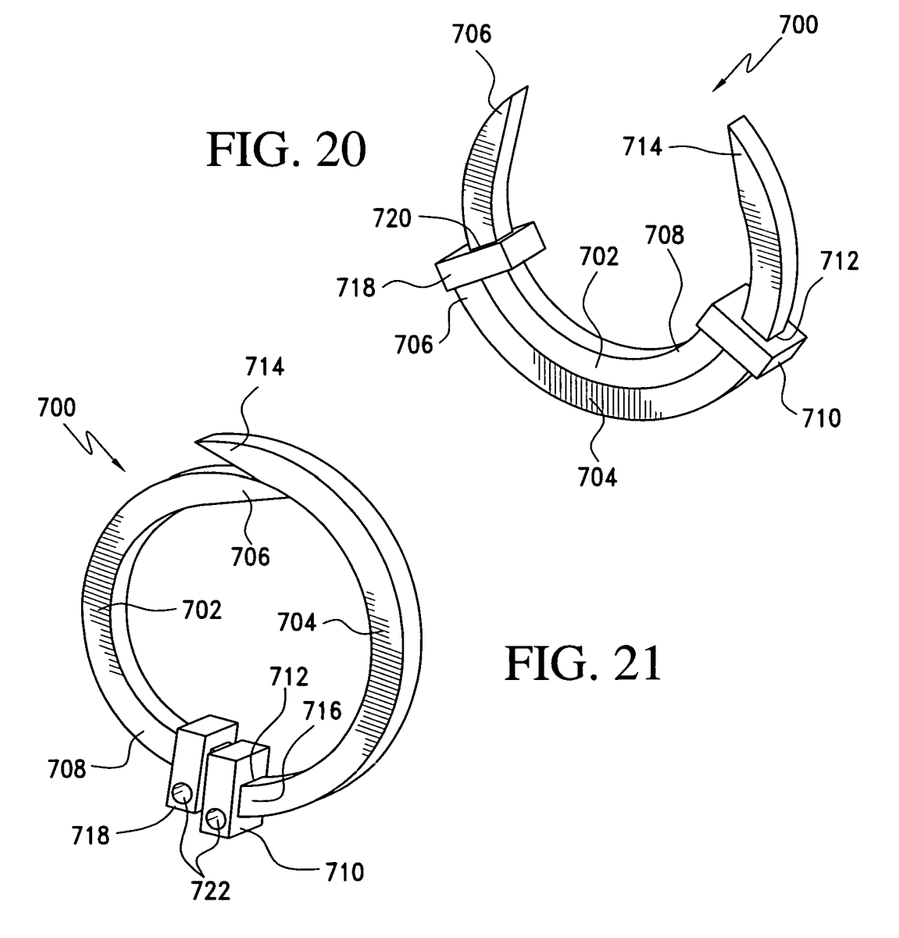

Referring to FIGS. 19, 20 and 21, a seventh embodiment of a fastener 700 in accordance with the present invention is disclosed. In accordance with this embodiment, the fastener 700 is composed of two semi-circular loops 702, 704 interrelated for closure and locking within the tissue of an individual. More particularly, the fastener 700 includes an inside first loop 702 and an outside second loop 704. The inside first loop 702 includes a first end 706 and a second end 708. The first end 706 is provided with a pointed tip shaped and dimensioned to function as an anchor member for penetration through the tissue of an individual. The second end 708 is provided with a locking member 710 having a locking aperture 712 shaped and dimensioned for the passage of the outside second loop 704 therethrough.

Similarly, the outside second loop 704 includes a first end 714 and a second end 716. The first end 714 of the outside second loop 704 is shaped and dimensioned for passage through the locking aperture 712 of the inside first loop 702. The first end 714 of the outside second loop 704 is further shaped and dimensioned as an anchor member for penetration through the tissue of an individual. The second end 716 of the outside second loop 704 includes an inwardly directed locking member 718 having a locking aperture 720 shaped and dimensioned for receiving the first end 706 of the inside first loop 702 in a manner permitting relative locking of the inside first loop 702 relative thereto.

In practice, the inside first loop 702 sits within the outside second loop 704 such that the inside first loop 702 and the outside second loop 704 conform to each other. As mentioned above, the first end 706 of the inside first loop 702 sits within the locking aperture 720 of the locking member 717 of the outside second loop 704 and the first end 714 of the outside second loop 704 sits within the locking aperture 712 of the locking member 710 of the inside first loop 702. In this way, the inside first loop 702 and the outside second loop 704 are securely held relative to each other but are permitted to rotate relative to each other as the first ends 706, 714 of the respective first and second loops 702, 704 pass through the locking members 710, 717 of the loops 702, 704.

In accordance with a preferred embodiment of the present invention, as the inside first loop 702 is rotated in a clockwise direction and the outside second loop 704 is rotated in a counterclockwise direction, the first ends 706, 714 of the respective first and second loops 702, 704 move toward each other while the locking members 710, 717 of the first and second loops 702, 704 also move toward each other at a position diametrically opposed to the meeting point of the first ends 706, 714 of the first and second loops 702, 704. When the first ends 706, 714 of the first and second loops 702, 704 meet, the locking members 710, 717 also meet forming a substantially circular configuration.

When the inside first loop 702 and the outside second loop 704 are rotated in this manner adjacent to tissue, the first ends 706, 714 of the first and second loops 702, 704 penetrate the tissue anchoring the fastener 700 therein. The locking members 710, 718 are locked relative to the respective loops 702, 704 using taper locks. Once the locking members 710, 718 are locked relative to the respective loops 702, 704 passing therethrough, the fastener 700 is securely held in position and the loop 702, 704 is securely coupled to the tissue.

The locking members 710, 718 are further provided with apertures 722 through which an instrument may be passed for facilitating mounting of the fastener 700 within the stomach tissue.

It is contemplated the various embodiments presented above may be provided with coatings to permit and/or enhance tissue ingrowth. The devices may also be coated with materials designed to prevent bacterial (biofilm) adhesion such as is commercially available. In addition, the size of the fasteners may be varied to achieve either temporary fixation (that is, the fastener only passes through the mucosa) or permanent fixation (that is, the fastener passes through the complete tissue).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A fastener for use during endoscopic procedures in which a suture is used in creating a predefined pouch through tissue apposition within the stomach, the fastener comprising:
   a spring biased, W-shaped fastener body including first and second anchors for selectively securing the fastener body to tissue, wherein the fastener includes a loaded position and a released position, and, upon release of the fastener from the loaded position, spring biased movement causes the fastener body to spring from the loaded position to the released position;
   the fastener body including inner first and second segments which are angularly oriented and coupled in a manner creating a connection aperture shaped and dimensioned for passage of a suture therethrough and outer third and fourth segments respectively angularly extending from the inner first and second segments and the first and second anchors extend from the outer third and fourth segments at angles transverse to longitudinal axes of the respective outer third and fourth segments; and
   wherein the outer third and fourth segments torsionally rotate relative to the inner first and second segments and along the longitudinal axes of the respective third and fourth segments upon release of the fastener held in the loaded position and spring biased movement from the loaded position to the released position.

2. A fastener for use during endoscopic procedures in which a suture is used in creating a predefined pouch through tissue apposition within the stomach, the fastener comprising:

a spring biased, W-shaped fastener body including first and second anchors for selectively securing the fastener body to tissue, wherein the fastener includes a loaded position and a released position, and, upon release of the fastener from the loaded position, spring biased movement causes the fastener body to spring from the loaded position to the released position;

the fastener body including inner first and second segments which are angularly oriented and coupled in a manner creating a connection aperture shaped and dimensioned for passage of a suture therethrough and outer third and fourth segments respectively angularly extending from the inner first and second segments, and the first and second anchors extend from the outer third and fourth segments at angles transverse to longitudinal axes of the respective outer third and fourth segments; and wherein the outer third and fourth segments rotate relative to the inner first and second segments and about axes substantially parallel to the longitudinal axes of the respective outer third and fourth segments upon release of the fastener held in the loaded position and spring biased movement from the loaded position to the released position.

3. A fastener for use during endoscopic procedures in which a suture is used in creating a predefined pouch through tissue apposition within the stomach, the fastener comprising:

a spring biased, W-shaped fastener body including first and second anchors for selectively securing the fastener body to tissue, wherein the fastener includes a loaded position and a released position, and, upon release of the fastener from the loaded position, spring biased movement causes the fastener body to spring from the loaded position to the released position;

the fastener body including inner first and second segments which are angularly oriented and coupled in a manner creating a connection aperture shaped and dimensioned for passage of a suture therethrough and outer third and fourth segments respectively angularly extending from the inner first and second segments, and the first and second anchors extend from the outer third and fourth segments at angles transverse to longitudinal axes of the respective outer third and fourth segments; and wherein the outer third and fourth segments torsionally rotate relative to the inner first and second segments and along the longitudinal axes of the respective third and fourth segments and the outer third and fourth segments rotate relative to the inner first and second segments and about axes substantially parallel to the longitudinal axes of the respective outer third and fourth segments upon release of the fastener held in the loaded position and spring biased movement from the loaded position to the released position.

\* \* \* \* \*